(12) United States Patent
Tucker et al.

(10) Patent No.: US 6,443,365 B1
(45) Date of Patent: Sep. 3, 2002

(54) DISCRIMINATING GROUND VEGETATION IN AGRICULTURE

(75) Inventors: Robert M Tucker, Binningup; Christopher C. Scott, Gingin, both of (AU)

(73) Assignee: Weed Control Australia Pty Ltd., Coogee (AU)

( * ) Notice: Subject to any disclaimer, the term of this patent is extended or adjusted under 35 U.S.C. 154(b) by 0 days.

(21) Appl. No.: 09/581,282

(22) PCT Filed: Dec. 8, 1998

(86) PCT No.: PCT/AU98/01018

§ 371 (c)(1), (2), (4) Date: Feb. 6, 2001

(87) PCT Pub. No.: WO99/30133

PCT Pub. Date: Jun. 17, 1999

(30) Foreign Application Priority Data

Dec. 8, 1997 (AU) .............................................. PP0781
Apr. 30, 1998 (AU) .............................................. PP3267

(51) Int. Cl.$^7$ .............................................. A01G 27/00
(52) U.S. Cl. ................... 239/69; 239/155; 239/159; 239/170; 47/1.7; 250/221.1
(58) Field of Search .................... 239/69, 170, 155, 239/159; 47/1.7, 1.01; 250/221.1, 226, 338.1

(56) References Cited

U.S. PATENT DOCUMENTS

| 4,015,366 A | * | 4/1977 | Hall, III ........................ 239/69 |
| 4,347,418 A | * | 8/1982 | Nobue et al. ................ 250/338.1 |
| 4,727,600 A | * | 2/1988 | Avakian ........................ 455/601 |
| 5,144,767 A | * | 9/1992 | McCloy et al. ................. 47/1.7 |
| 5,222,324 A | * | 6/1993 | O'Neall et al. ................. 47/1.7 |
| 5,606,821 A | * | 3/1997 | Sadjadi et al. ................. 47/1.7 |
| 5,623,259 A | * | 4/1997 | Giangardella ............... 340/932.2 |
| 5,793,035 A | * | 8/1998 | Beck et al. ................. 250/222.1 |
| 5,818,339 A | * | 10/1998 | Giles et al. ................... 340/583 |

* cited by examiner

Primary Examiner—Lesley D. Morris
Assistant Examiner—Dinh Q. Nguyen
(74) Attorney, Agent, or Firm—Fulbright & Jaworski L.L.P.

(57) ABSTRACT

A method and device for discriminating different types of ground vegetation in agriculture is disclosed in which an artificial source (24) of electromagnetic radiation is employed for directing a beam (26) of radiation onto the vegetation. A sensor assembly (30) is provided for detecting reflected radiation from the vegetation in a selected frequency band and generating a sensing signal in response to the detection. A logic controller (32) determines whether a magnitude of the sensing signal falls within a predetermined range of values in order to distinguish one type of vegetation from another type. In the near infred region of the electromagnetic spectum different types of weeds absorb significantly less infra-red radiation than other types of vegetation. Logic controller (32) compares the amplitude of the sensing signal with a decision window. If the amplitude of the incoming sensing signal falls within the decision window then the logic controller (32) determines that a certain type of plant has been detected and activates the corresponding solenoid valve (36) to deliver dose of spray liquid from spray nozzle (14) to the targeted weed (28).

20 Claims, 6 Drawing Sheets

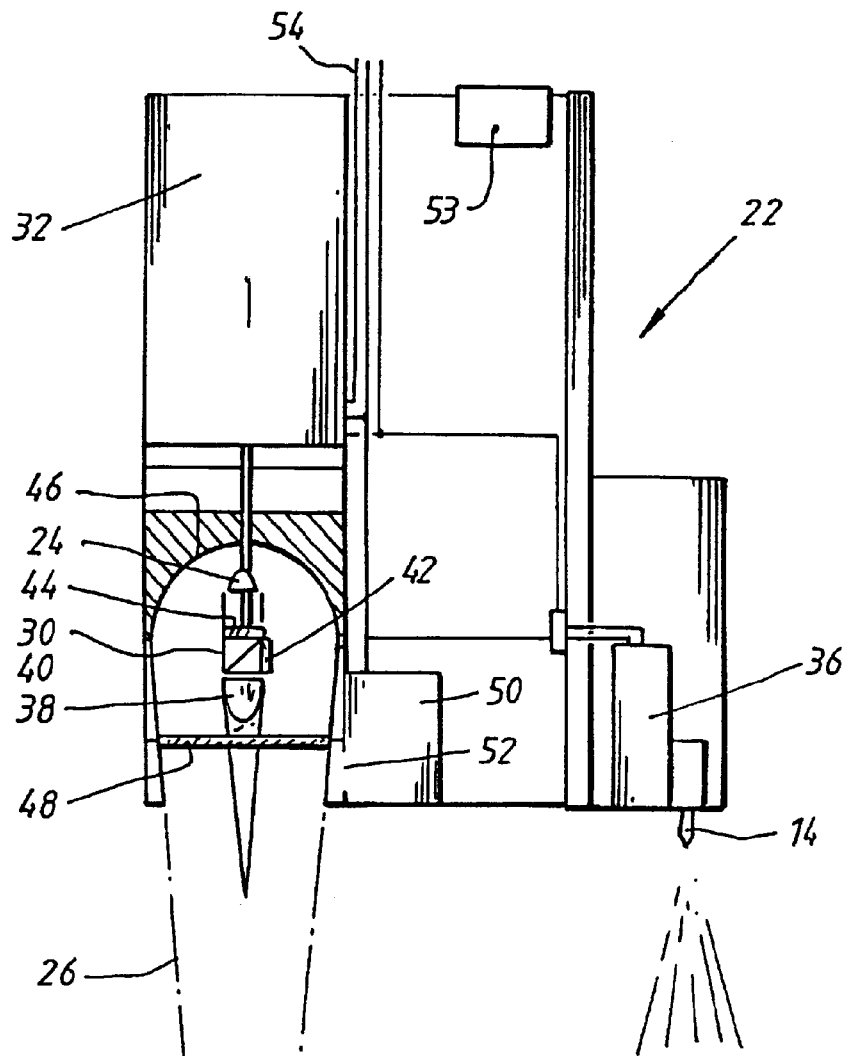
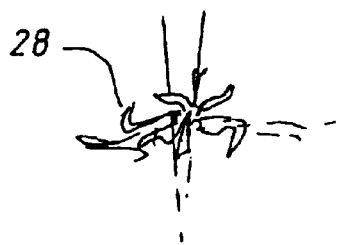

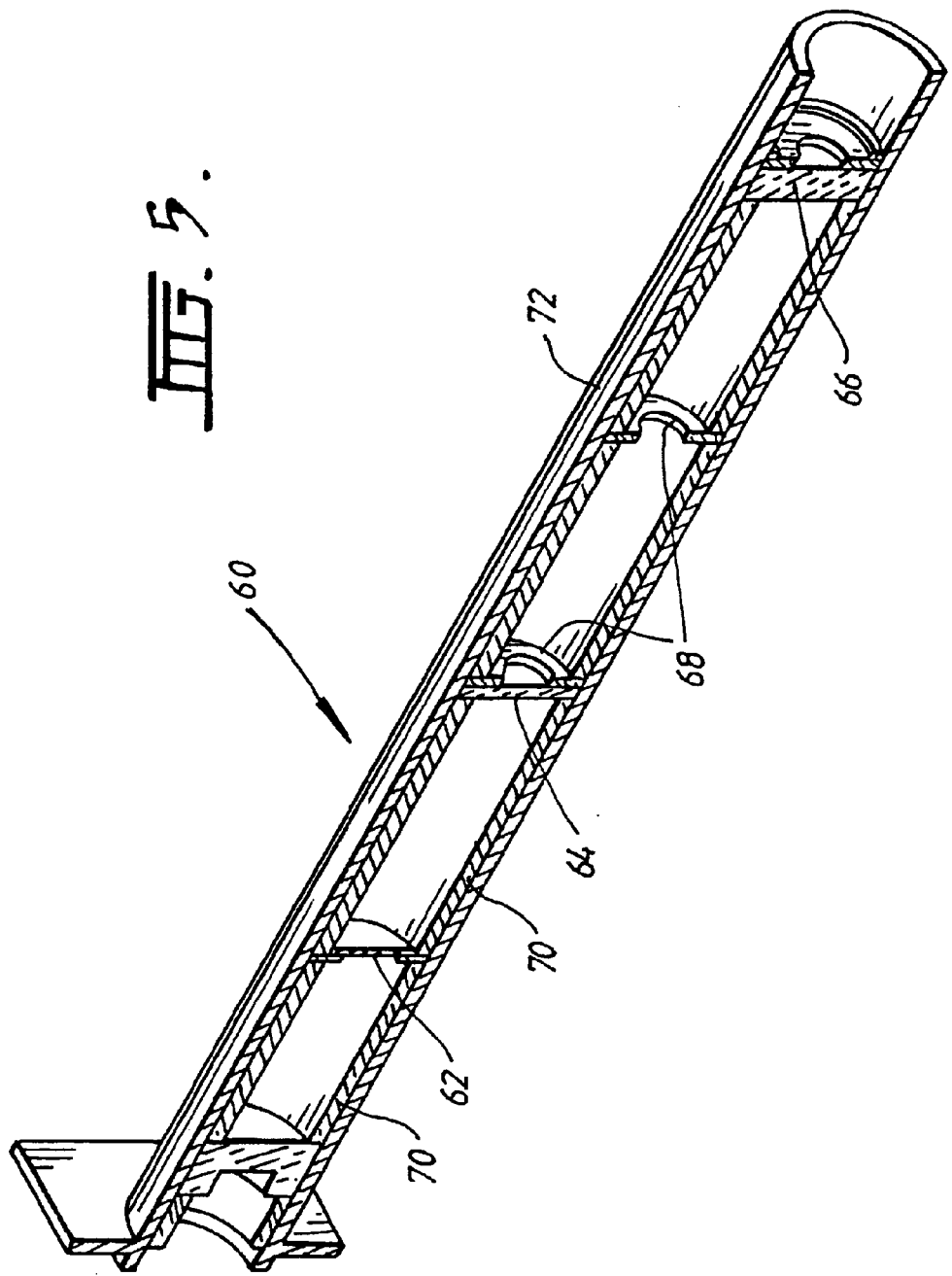
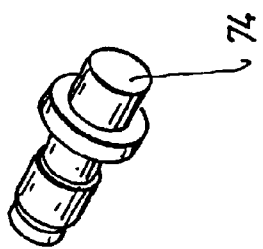
FIG. 5.

DISCRIMINATING GROUND VEGETATION IN AGRICULTURE

FIELD OF THE INVENTION

The present invention relates to a method and device for discriminating different types of ground vegetation in agriculture and relates particularly, but not exclusively, to an agricultural spraying apparatus which incorporates such a device. Whilst the invention will be described with particular reference to an agricultural spraying apparatus for spraying herbicides, it will be appreciated that the same method and device for discriminating different types of ground vegetation may be employed in other applications, for example, for applying fertilisers, or other pesticides, and for conducting surveys of ground vegetation.

In its application to the spraying of agricultural herbicides the device can provide the following advantages over known techniques for discriminating ground vegetation. The process of distinguishing different types of ground vegetation or coverage can be effected independently of ambient light conditions, ie, varying sunlight conditions will not affect the readings. Signal processing is very rapid as only a single comparison of values is made, thus facilitating rapid decision making on-the-fly. No monitoring of ground speed is required as each spray nozzle is activated for the duration of sensing the presence of a weed in the target area only. The volume per acre of herbicide required can be vastly reduced as the application of herbicide is precisely targeted to weeds only. Refilling of the tank on the boom spray is thus also minimised.

BACKGROUND TO THE INVENTION

Over the last couple of decades broadacre spraying has become an essential component of crop management on most farms in Australia. Chemical companies have developed new chemical pesticides for killing weeds, insect pests and diseases which attack cash crops. The most commonly used technique for broadacre spraying of pesticides is the use of boom sprays, which may be self-propelled or towed behind another vehicle. A typical boom spray has a plurality of spray nozzles mounted at spaced locations along a boom, a. large tank for containing the spray liquid and a pump system for pumping the liquid to the nozzles. A control system is often provided for controlling the rate at which the pesticide is sprayed relative to ground speed, and a marker system may be used to aid driving and avoid overlapping.

One of the disadvantages of conventional boom sprays is that herbicides are sprayed indiscriminately on both the crop, bare ground and weeds. This is of concern in the case of food crops, with consumer groups becoming increasingly vocal about chemical residue in crops and livestock. There is also an economic disincentive since a much greater volume of chemical spray must be applied per acre than is actually required to effectively control the weeds.

Various attempts have been made to allow for more discriminate spraying of herbicides. U.S. Pat. No. 5,144,767 discloses a controller for agricultural sprays developed by The Division of Plant Industries, New South Wales Agriculture and Fisheries. U.S. Pat. No. 5,144,767 discloses an agricultural spray which is controlled by an apparatus having a sensor for determining the irradiance in the red and near infra-red bands of the electromagnetic spectrum, and a plurality of sensors for determining the radiance of a target area in the red and near infra-red wave bands. A controller controls the individual sprays by comparing the ratios of the radiance to the irradiance (reflectance) in each band respectively, and determining if the spray for a particular target area should be turned on or off. The determination may be made by referring to a stored look-up table of reflectance values, or by carrying out the calculations of non-linear decision algorithms. Reflectance is defined as the ratio of reflected energy to incident energy.

In U.S. Pat. No. 5,144,767 reflectance is adopted as the decision-making criteria, rather than radiance, in order to overcome problems in the variability of radiance measurements caused by changing ambient light conditions. In direct sunlight a significant component of the irradiance (incident sunlight) on the earth's surface is in the red and near infra-red wave bands. However, in cloudy conditions there is a significant decrease in the amount of infra-red radiation reaching the Earth's surface due to absorption by atmospheric moisture and clouds. It is thought that reflectance should stay approximately the same under varying light conditions for a particular target. Nevertheless, in practice there can still be considerable variability in the calculated reflectance value as the amount of sunlight irradiating the target area will vary relative to the amount of sunlight irradiating the irradiance sensor. This occurs because the target area is located underneath the apparatus and will therefore intermittently be in shadow and in direct sunlight, depending on the direction of travel of the boom spray.

SUMMARY OF THE INVENTION

The present invention was developed with a view to providing an improved device and method for discriminating different types of ground vegetation that is more reliable than prior art techniques.

According to one aspect of the present invention there is provided a device for discriminating different types of ground vegetation, the device comprising:

- an artificial source of electromagnetic radiation for directing a beam of radiation onto the vegetation;
- a plurality of sensors for detecting radiation from said radiation source reflected onto each of said sensors from the vegetation in a selected frequency band and generating a sensing signal from each sensor in response to said detection, and wherein said plurality of sensors are arranged in a sensor array with a geometric configuration adapted to aid in discriminating different types of vegetation; and,
- signal processing means for determining whether a magnitude of each said sensing signal falls within a predetermined range of values whereby, in use, one type of vegetation can be distinguished from another type based on the magnitudes of said sensing signals.

Preferably the device further comprises a shroud for minimising the amount of sunlight reflected from the vegetation.

In a preferred embodiment said selected frequency band is in the infra-red portion of the electromagnetic spectrum, and said predetermined range of values is set to enable a type of weed plant to be distinguished from a crop plant. Preferably said selected frequency band is in the infra-red portion of the spectrum having a wavelength within the range of 450 nm to 10 $\mu$m. The most preferred frequency band is in the near infra-red waveband of approximately 650 nm to 2000 nm.

Preferably said artificial radiation source produces a beam of substantially collimated light. Typically said sensor is a photodiode adapted to provide a sensing signal in response to detected radiation in the near infra-red wave band. Preferably sensors capable of providing a sensing signal in response to detected radiation in the visible and/or ultraviolet (UV) wave bands are also employed.

Preferably said signal processing means determines whether a magnitude of the sensing signal falls within a predetermined range of values (a sensing window) which is specific to each sensor in the sensor array. Preferably each sensor in the sensor array has a sensing window that is unique to that sensor.

According to another aspect of the present invention there is provided a method for discriminating different types of ground vegetation, the method comprising:

directing a beam of electromagnetic radiation from an artificial source onto the vegetation;

providing a plurality of sensors arranged in a sensor array with a geometric configuration adapted to aid in discriminating different types of vegetation;

detecting radiation from said artificial source reflected from the vegetation onto each of said sensors in a selected frequency band and generating a sensing signal from each sensor in response to said detection; and, determining whether a magnitude of each said sensing signal falls within a predetermined range of values whereby, in use, one type of vegetation can be distinguished from another type based on the magnitude of said sensing signals.

Preferably the method further comprises the step of:

shading the vegetation from direct sunlight so as to minimise the amount of sunlight reflected from the vegetation.

According to a still further aspect of the present invention there is provided an agricultural spraying apparatus for spraying ground vegetation, the apparatus comprising:

a spraying means for delivering a liquid spray to ground vegetation;

an artificial source of electromagnetic radiation for directing a beam of radiation onto the vegetation;

a plurality of sensors for detecting radiation from said radiation source reflected onto each of said sensors from the vegetation in a selected frequency band and generating a sensing signal from each sensor in response to said detection, and wherein said plurality of sensors are arranged in a sensor array with a geometric configuration adapted to aid in discriminating different types of vegetation; and, signal processing means operatively connected to said sensor array and spraying means for determining whether a magnitude of each said sensing signal falls within a predetermined range of values, and for actuating said spraying means when a particular type of vegetation is distinguished from another type based on the magnitudes of said sensing signals.

Preferably the apparatus further comprises a shroud for shading the vegetation and minimising the amount of sunlight reflected from the vegetation.

Typically said spraying means includes a plurality of spray nozzles and a corresponding plurality of electromagnetically actuated valves for controlling the delivery of said liquid spray through each nozzle. Advantageously said radiation source and sensor are one set of a plurality of sets of radiation sources and sensors, a respective set being provided adjacent each of said spray nozzles.

BRIEF DESCRIPTION OF DRAWINGS

In order to facilitate a more detailed understanding of the nature of the invention an embodiment of a device and method for discriminating different types of ground vegetation will now be described in detail, by way of example only, with reference to the accompanying drawings in which:

FIG. 3 is a schematic illustration of a second embodiment of the device for discriminating different types of ground vegetation;

FIG. 5 is an isometric section view through another embodiment of a sensor assembly;

DETAILED DESCRIPTION OF PREFERRED EMBODIMENTS

Figure 1:
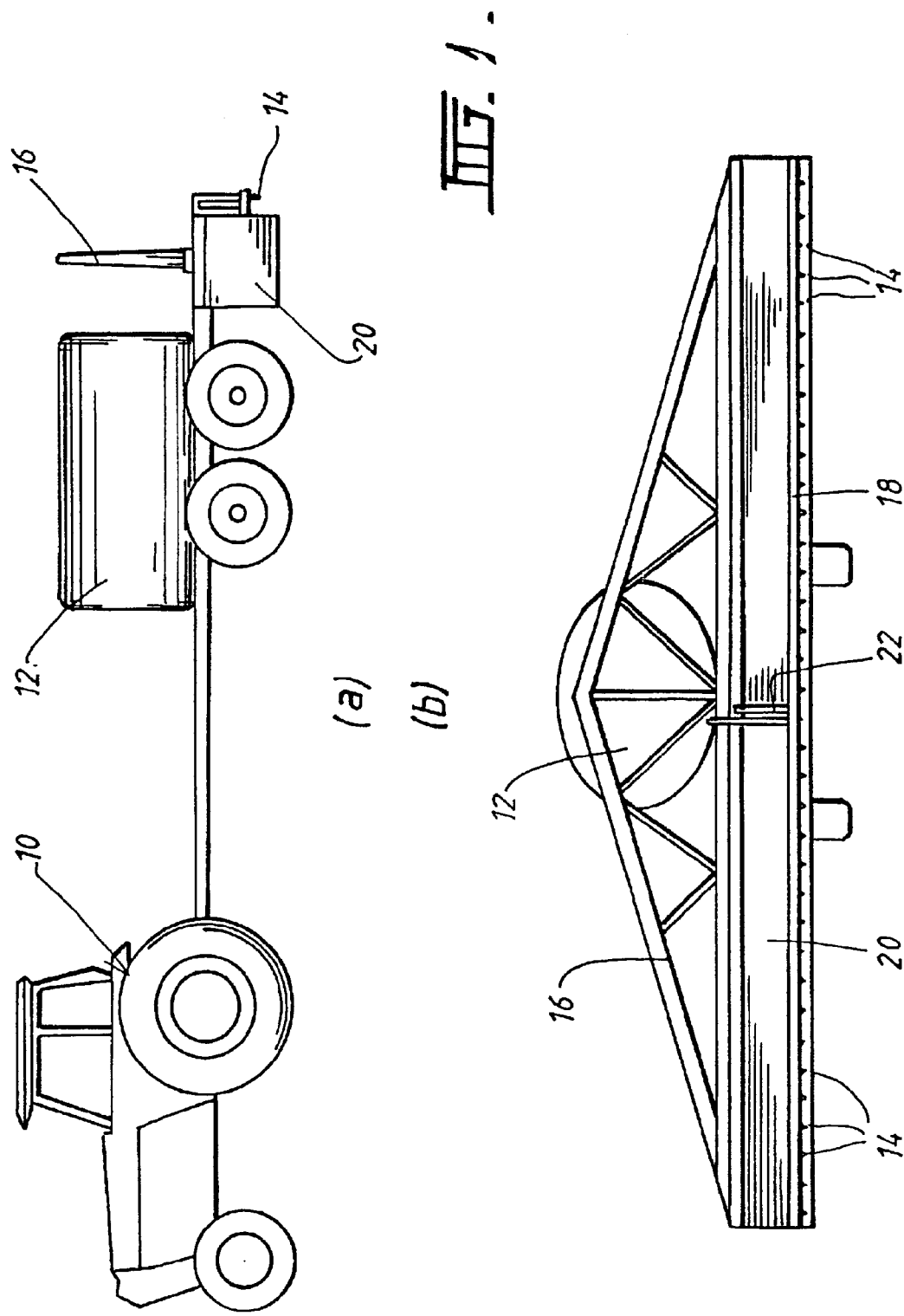
FIGS. 1(a) and (b) illustrate a boom spray which incorporates an embodiment of a device for discriminating different types of ground vegetation in accordance with the present invention.

FIGS. 1(a) and (b) illustrate a typical agricultural spraying apparatus known as a boom spray, in this case of the kind which is towed behind another vehicle, tractor 10. The boom spray is in the form of a trailer on which is mounted a large tank 12 for containing the spray liquid, typically a herbicide or other chemical pesticide. A pump system (not shown) pumps the spray liquid to a plurality of nozzles 14 mounted at spaced locations along a transversally mounted boom 16. A spray liquid supply line 18 which extends the full length of the boom supplies the herbicide to each of the spray nozzles 14. A device 22 for discriminating different types of ground vegetation is mounted on the boom spray and controls the delivery of spray liquid from the nozzles 14 depending on the type of vegetation distinguished by the device.

Figure 2:
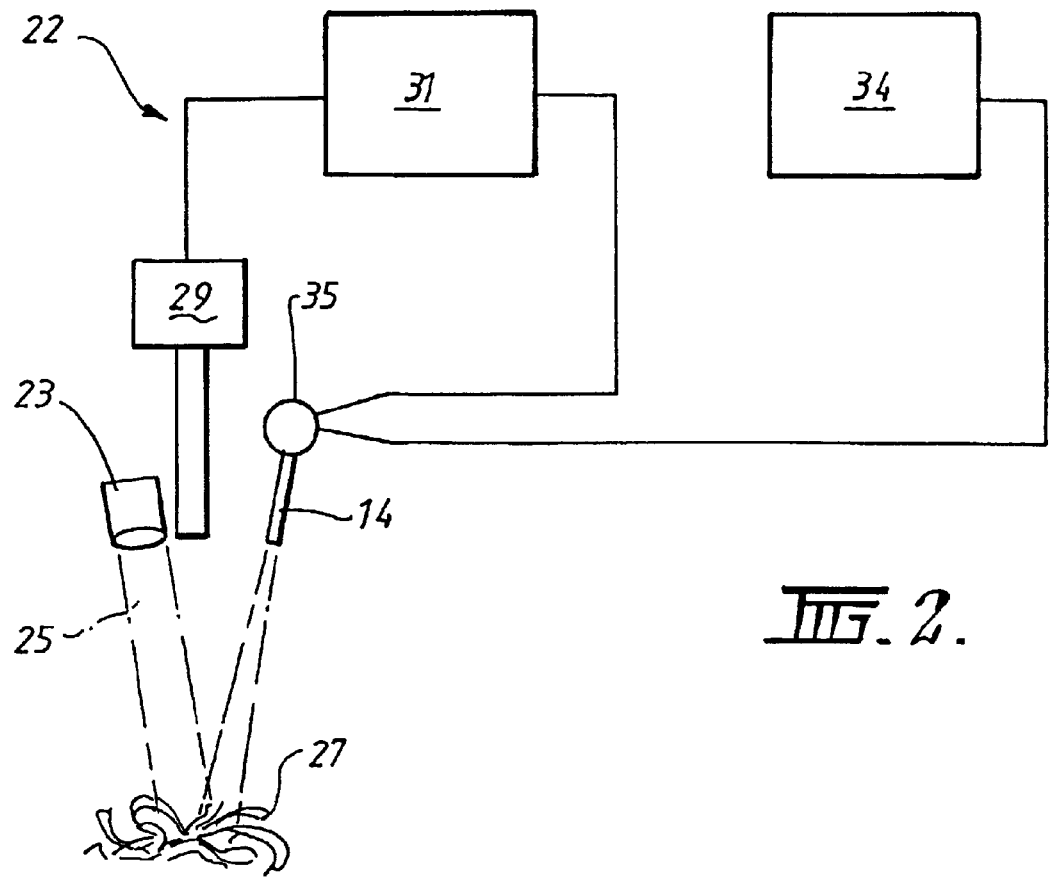
FIG. 2 is a schematic illustration of a first embodiment of the device for discriminating different types of ground vegetation employed in the boom spray of FIG. 1.

One embodiment of the device 22 for discriminating different types of ground vegetation is illustrated schematically in FIG. 2. The device 22 comprises an artificial source 23 of electromagnetic radiation for directing a beam 25 of radiation onto the vegetation 27. In this embodiment, the radiation source 23 is a wide-spectrum quartz halogen lamp having a lens for focussing the beam 25 of radiation onto the vegetation. A sensor assembly 29 for detecting radiation from the lamp 23 reflected from the vegetation in a selected frequency band is also provided. In this embodiment, one or more filters are employed to allow radiation in selected frequency bands to pass therethrough to the sensor assembly 30. Sensors in the sensor assembly 30 generate a sensing signal in response to detection of the reflected radiation.

The device 22 also includes a signal processing means, in this case in the form of a logic controller 31 for determining whether a magnitude of the sensing signal from the sensor assembly 29 falls within a predetermined range of values. The predetermined range of values or decision window is programmed into the logic controller so that it is able to distinguish one type of vegetation from another type based on the magnitude of the sensing signal from the sensor assembly 30. In this connection, "magnitude" may refer to the frequency and/or amplitude of the sensing signal. A pump and chemical supply system 34 delivers the spray liquid to each of the spray nozzles 14. Each of the spray nozzles 14 is provided with a solenoid controlled valve 35 for controlling the delivery of spray liquid from each nozzle. The solenoid controlled valves 35 are also under the control of logic controller 31. Hence, when the logic controller 31 detects the presence of, for example, a weed on the basis of the sensing signal generated by sensor assembly 29, it activates the solenoid controlled valve 35 to release a Jet of spray liquid from the nozzle 14 onto the weed.

Preferably a shroud 20 is suspended from the boom 16 as shown in FIG. 1, in order to minimise the amount of sunlight which might reach the sensors and interfere with the detection of reflected radiation. Shroud 20 is made from a flexible, light-impervious material and is of sufficient length to shade any vegetation directly below the lamp 23 and sensor assembly 29 from direct sunlight throughout most of the day. If spraying is done after dark, the shroud 20 may be dispensed with.

Preferably the boom 16 is designed to stay at a fairly constant height as it travels over the ground, so as to minimise variations in the intensity of the reflected radiation due to changes in the distance of the radiation source and sensor assembly from the ground vegetation. Preferably, the sensor assembly is maintained at a height of between 10 mm to 500 mm above the target vegetation, more preferably between 200 mm to 400 mm above the target vegetation. Although it has been found that the magnitude of the sensing signal does vary with changes in height, these variations are smaller than the difference in magnitude produced by the absorption of electromagnetic radiation by different types of vegetation in selected frequency bands.

Only one radiation source 24 and sensor assembly 30 are visible in FIG. 2. However, preferably a plurality of sets of radiation sources and sensors are provided on the boom spray, each set being located adjacent a respective spray nozzle 14 in order to discriminate the type of vegetation in the target area of each spray nozzle 14.

The target area, namely, the area on the vegetation which is irradiated by the radiation source is preferably quite small, typically between 5 mm to 100 mm, more preferably 10 mm to 60 mm in diameter. Since the sensor is effectively measuring the intensity of reflected radiation, it is desirable that this measurement should be largely unaffected by variations in the distance between the sensor and the vegetation. The intensity of radiation from a point source is inversely proportional to the square of the distance from the source, as the electromagnetic waves radiate radially from the point source. Therefore, in order to eliminate or substantially reduce the effect of the inverse square law, it is preferred to use a substantially collimated radiation source, from which a parallel or near parallel beam of radiation can be obtained. Alternatively, a focussed beam of radiation with a relatively long focal length may be employed.

Another embodiment of the device 22 for discriminating different types of ground vegetation is illustrated schematically in FIG. 3. The device 22 comprises an artificial source 24 of electromagnetic radiation for directing a beam 26 of radiation onto the vegetation 28. A sensor assembly 30 for detecting radiation from the radiation source 24 reflected from the vegetation in a selected frequency band is also provided. Sensor assembly 30 generates a sensing signal in response to detection of the reflected radiation.

The device 22 also includes a signal processing means, in this case including a micro-processor based controller 32 for determining whether a magnitude of the sensing signal from sensor assembly 30 falls within a predetermined range of values. The predetermined range of values or decision window is programmed into the controller 32 so that it is able to distinguish one type of vegetation from another type based on the magnitude of the sensing signal from sensor assembly 30. A pump and chemical supply system (not illustrated) delivers the spray liquid to each of the spray nozzles 14. Each of the spray nozzles 14 is provided with a solenoid controlled valve 36 for controlling the delivery of spray liquid from each nozzle. The solenoid controlled valves 36 are under the control of controller 32. Hence, when controller 32 detects the presence of, for example, a weed on the basis of the sensing signal generated by sensor assembly 30, it activates the solenoid controlled valve 36 to release a jet of spray liquid from the nozzle 14 onto the weed.

Figure 4:
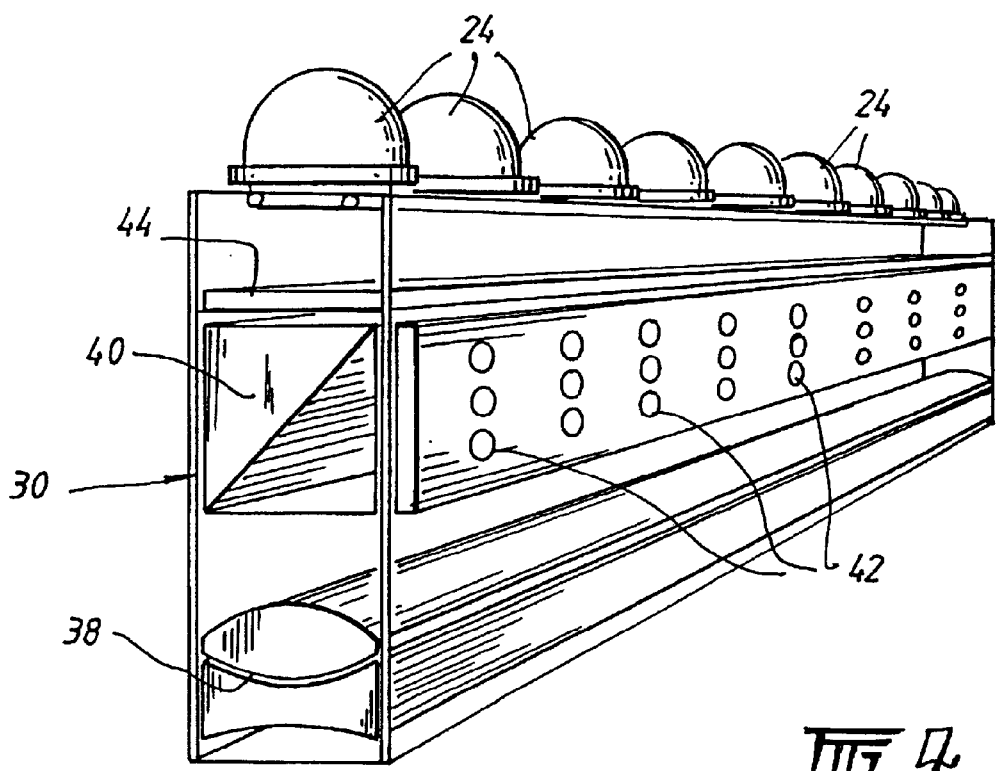
FIG. 4 illustrates a sensor assembly and LED array used in the device of FIG. 3.

In this embodiment, as can be seen more clearly in FIG. 4, the radiation source 24 is a plurality of light emitting diodes (LEDs) mounted on top of the sensor assembly 30. The sensor assembly 30 comprises a lens 38, a splitter 40 and two sensor arrays 42 and 44 respectively. Splitter 40 splits the reflected radiation from beam 26 into two orthogonal beams which strike the sensor arrays 42, 44 respectively. As can be seen most dearly in FIG. 4, the two sensor arrays 42, 44 are mounted substantially perpendicular to each other. Lens 38 focuses the reflected beam of radiation onto the respective sensor arrays 42, 44 via splitter 40.

The use of two sensor arrays can provide for greater accuracy and flexibility in target identification. For example, in the identification of skeleton weed, the second sensor array 42 can be used to detect the presence of green vegetation hence eliminating the false reading effect of high infra-red (IR) reflectance of stubble. The two sensor system can provide accurate negative selection. Negative selection is the process of isolating the crop from any other vegetation and in the application of selected weed spraying, applying spray to the weed only. This may be difficult using a single sensor because no comparison can be made between the ground, stubble and weeds that require spraying. With two sensor arrays, electronic logic components such as a NAND gate can be incorporated to provide for negative selection. NAND is short for "not-and". In the context of negative selection, it can be applied as "not the crop and a specific frequency", for example, "not the IR and shape component of a wheat leaf and must be green". This control logic is provided in the controller 32.

A parabolic mirror 46 is provided to provide a focussed beam of light 26 from the LEDs 24 with a long focal length. There is a reading zone of the light beam 26 within which the sensor assembly 30 is able to detect the reflected radiation and generate a sensing signal in response to the detection. The base of the reading zone is determined by the point where the footprint of the light beam is smaller than the size of the sensor, typically approximately 7 mm. At its upper end, (closest to the sensor assembly 30) the reading zone is limited by the length of the shadow zone created by the shadow of the sensor assembly 30 itself. The full length of the reading zone is dependent on the angle of convergence of the parabolic mirror 46 and the distance of the LEDs 24 from the surface of the parabola. This distance is set to compensate for the loss of reflected light from the target as the target distance increases from the sensor assembly 30 in accordance with the inverse square law. Thus the length and position of the reading zone can be varied by changing the size of the aperture of the parabolic mirror 46. The light beam 26 does not have to totally compensate for the inverse square law, as long as it provides accuracy within the tolerances of the difference in readings between the target plants and the surrounding vegetation. The balance between the optimum length of the reading zone and decreasing the accuracy due to broader divergence of light, can be readily determined by using an adjustable bench-mounted prototype.

As can be seen more clearly in FIG. 4, LED 24 is one of an array of LEDs mounted on an integrated sensor assembly 30 which incorporates a single elongate lens 38, a single elongate splitter 40 and a plurality of sets of sensor arrays 42,44 as shown more clearly in FIG. 4. The parabolic mirror 46, sensor assembly 30 and array of LEDs 24 are protected from the environment by a transparent window 48. A fan 50 blows a continuous supply of air through vents 52 over the external surface of the window 48 to remove any dust or debris which may accumulate on window 48 and interfere with the correct operation of the light beam 26 and sensor assembly 30. Air filter 52 filters air drawn into the enclosure housing the device. Cables 54 allow connection to an external power source and the transfer of data to and from the controller 32 and an external computer.

The present inventors have found that in selected frequency bands the absorption of electromagnetic radiation varies significantly for different types of ground vegetation. For example, in the near infra-red region of the electromagnetic spectrum different types of weeds absorb significantly less infrared radiation than other types of vegetation. Without wishing to be bound by theory, it is thought that this may be due to variations in the moisture content of the plant, variations in colour and width of the leaves of the plant and differences in the surface texture of plant leaves. Depending on the amount of radiation reflected from the ground vegetation, the sensing signal generated by sensor 30 will vary in amplitude. The logic controller 32 compares the amplitude of the sensing signal with the decision window programmed into the controller 32. If the amplitude of the incoming sensing signal falls within the decision window then the controller 32 determines that a certain type of plant has been detected and activates the corresponding solenoid valve 36 to deliver a dose of spray liquid to the targeted weed.

Figure 6:
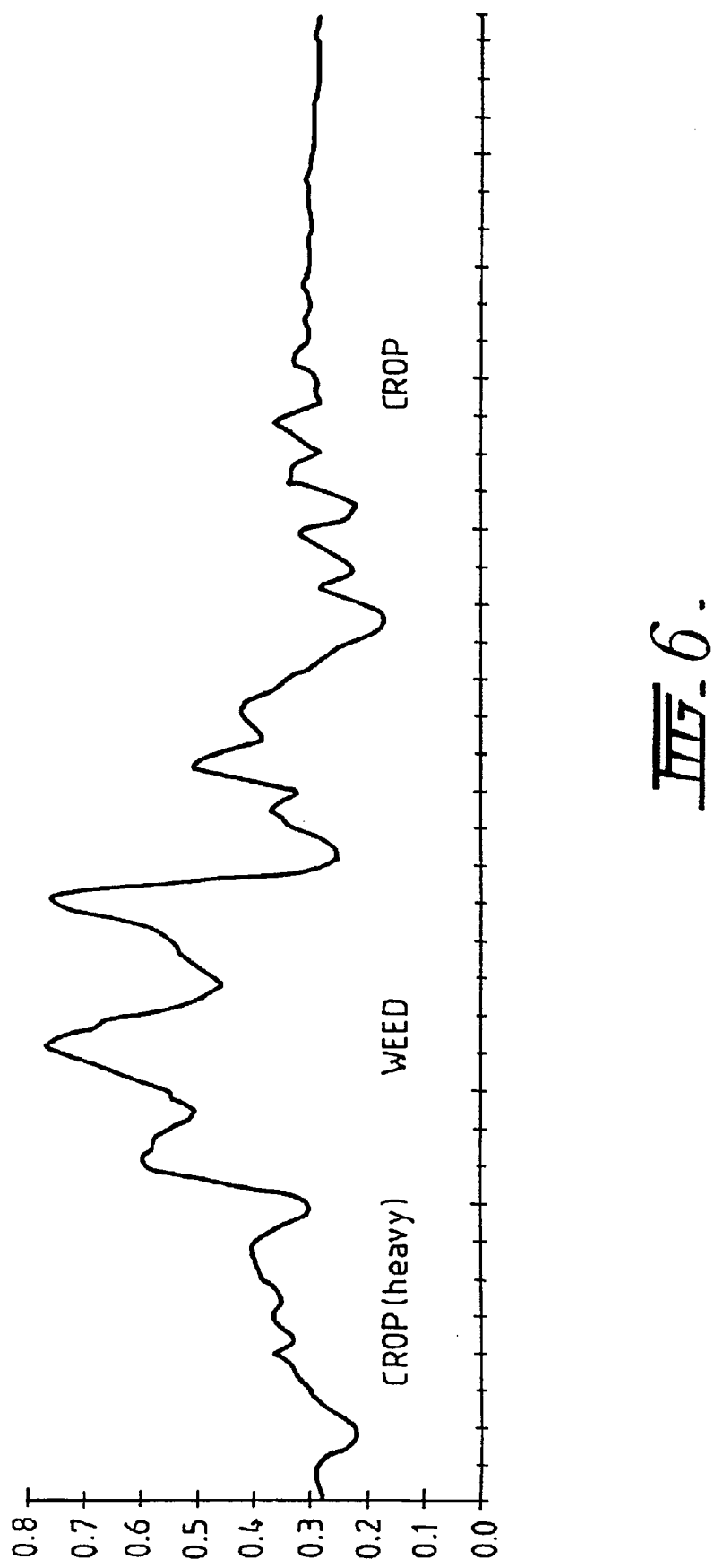
FIG. 6 is a graph of the variation in magnitude of the sensing signal generated by the device of FIG. 2 for different types of ground vegetation; and, FIGS. 7, 8 and 9 illustrate a variety of sensor arrays that may be employed in the device for discriminating different types of ground vegetation in accordance with the invention.

In trials to date, a radiation source has been used which provides a beam of radiation that includes a portion of the infra-red wave band. The sensors employed in the trial apparatus are photodiodes designed to detect infra-red radiation having a peak response wavelength of between approximately 900 nm to 1000 nm. The inventors have found that at these wavelengths a variety of different types of weeds and crop plant can be readily distinguished. FIG. 6 illustrates variations in the magnitude of the sensing signal generated by the photodiode in response to reflected infra-red radiation from different types of ground vegetation and coverage. As can be seen in FIG. 6 the two main leaves of a weed (Cape Weed) appear as two easily distinguishable peaks in the graph of output voltage from the photodiode, relative to the signal level from the surrounding crop plants. With the type of weed producing a sensing signal with amplitudes represented in FIG. 6 the range of values employed as a decision window by the controller would be, for example, from approximately 0.6 to 0.9 volts. Whenever the sensing signal produced by the photodiode has an amplitude which falls within this range of values, the controller will activate the corresponding solenoid valve to release a spray of herbicide from the spray nozzle onto the weed in the target area.

FIG. 5 illustrates another embodiment of a sensor assembly 60 for focussing the reflected radiation from a constant footprint onto a sensor head 74. The assembly 60 includes a series of three lenses 62, 64 and 66 which converge and focus the reflected radiation in such a manner that the sensor head always "sees" a footprint on the target vegetation of approximately 12 mm in diameter. A series of spacers 68 and 70 are used to precisely locate the lenses 62, 64 and 66 at predetermined positions along the length of a tube 72 which houses the sensor assembly. A sensor head 74 plugs into one end of the tube 72. Spacers 68 also act as reflected light buffers, preventing the reflection of unwanted light from the inner wall of tube 72 into the sensor head 74. Using the sensor assembly 60 a focussing of the reflected radiation can be obtained which results in substantially no detectable variation in the size of the read footprint on the target vegetation when the distance between the sensor assembly and the target vegetation is varied from between 10 to 500 mm.

Any other suitable source of radiation may be employed, for example, a laser and/or optical fibres. Optical fibre may also be used to direct the reflected radiation onto the sensor. The power consumption may be significantly reduced by employing a radiation source adapted to radiate electromagnetic waves within the required portion of the electromagnetic spectrum only, for example, within the near infra-red portion of the electromagnetic spectrum. Both the radiation source and the sensor can be selected, or employed with a filter, to obtain an optimum variation in the magnitude of the sensing signal for different types of vegetation. Thus, for example, in some crops there are two different types of plant which can only be distinguished by the colour of the flowers. If it is desired to distinguish the one type of plant from the other, it may be necessary to employ electromagnetic radiation within the visible light spectrum in order to distinguish the different colours of the flowers. In other applications, it may be desirable to employ electromagnetic radiation from the ultra-violet portion of the electromagnetic spectrum. Any other suitable sensor may be employed apart from a photodiode, for example, a charge coupled device (CCD) sensor.

In the embodiment of FIGS. 3 and 4, the frequency of the radiation can be adjusted in a number of ways. Firstly, the source of radiation can be varied by alternating different wave length LEDs in the array, for example, using an 880 nm LED and a 450 nm LED alternately down the length of the array as illustrated in FIG. 4. A second way to adjust the radiation frequency is to place filters between the lens and the splitter, or between the splitter and the sensor arrays. Each of the sensor arrays 42, 44 includes a plurality of sensors arranged in a particular geometric configuration designed to facilitate discrimination of different types of ground vegetation, as will be described in more detail below with reference to FIGS. 7 to 9.

Advantageously, the device may include a calibration unit (not illustrated) for calibrating the range of values employed as decision windows by the logic controller. There may in fact be more than one decision window in order to distinguish different types of weed or crop plant which may occur in the same paddock. The calibration unit includes a radiation source and sensor identical to that employed on the boom spray, and is held over a type of plant desired to be distinguished from other types of plants in order to obtain a reading for calibration purposes. The unit may include means for varying the wavelength of the radiation in order to optimise the magnitude of the sensing signal generated by the senor in response to reflected radiation.

The sensor assembly may employ a plurality of sensors arranged in an array with a geometric configuration adapted to aid in discriminating different types of vegetation. FIGS.

Figure 7:
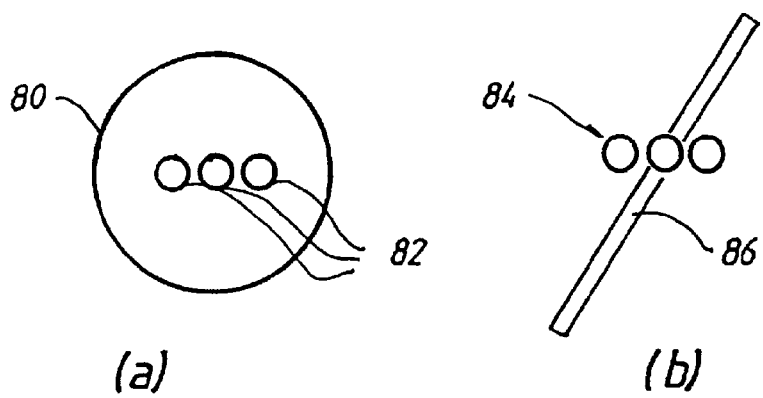
Figure 8:
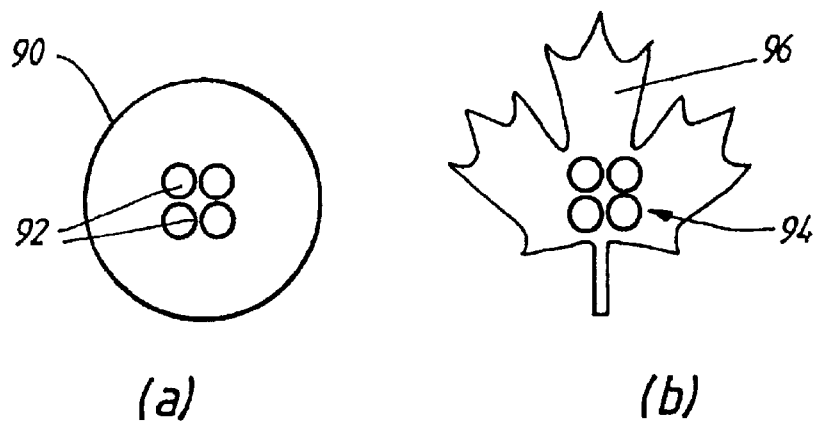

7, 8 and 9 illustrate examples of three different sensor arrays that may be employed in the sensor assembly. In FIG. 7 a sensor head array 80 having a row of three sensors 82 arranged in a linear array is illustrated. FIG. 7(a) illustrates the geometric configuration of the sensors 82 in the sensor array, whereas FIG. 7(b) illustrates the read footprint 84 of the linear array of sensors on the target vegetation 86. The linear array of sensors is adapted to distinguish a stem type target vegetation such as, for example, skeleton weed. The sensing signals generated by all three sensors 82 are read simultaneously by the logic controller. In this example, the plant stem 86 provides an output from sensor 2 of 1.7 volts. The adjacent sensors 1 and 3 provide outputs of 1.0 and 0.9 volts respectively. A unique decision window for each sensor 82 is programmed into the controller in order to detect sensing signals which fall within the following predetermined ranges of values:

sensor 1—0.9 to 1.1 volts
sensor 2—1.6 to 1.8 volts
sensor 3—0.8 to 1.0 volts When a plant passes under the sensor unit and the sensing signals from all three sensors fall within the upper and lower limits of the respective decision windows, then the logic controller determines that a match has been found and is able to distinguish the type of vegetation as a stem type vegetation. By providing each sensor with a unique decision window and setting the decision windows for sensors 1 and 3 at lower levels than the decision window for sensor 2, the logic controller will not mistakenly identify a broad leaf plant since the sensing signals from sensors 1 and 3 must be of reduced amplitude compared to the sensing signal of sensor 2. FIG. 8 illustrates another sensor array with a geometric configuration adapted to identify broad leaf type target vegetation such as, for example, wild radish rosette. In this embodiment the sensor array 90 has an array of four sensors 92 arranged in a rectangular configuration as shown in FIG. 8(a). FIG. 8(b) illustrates the read footprint 94 on the target vegetation 96. In this sensor array 90 each of the sensors 92 must produce an output sensing signal which falls within a decision window which has the same upper and lower limits for each of the sensors 1, 2, 3 and 4. The logic controller will only identify the target vegetation as a broad leaf plant if all four sensing signals fall within the decision window.

FIGS. 7 and 8 illustrate the manner in which the geometric configuration of sensors in a multi-sensor array can be used to discriminate different types of plant vegetation based on the shape of the vegetation. The multi-sensor array may also be used to more accurately determine a particular plant's "radiation signature". A plant's "radiation signature" are the specific electromagnetic frequencies of radiation that the plant reflects enabling discrimination from other foliage. Each of the sensors in a multi-sensor head or sensor assembly can be designed to detect a specific wavelength by either using frequency specific sensors or filtered sensors. A decision window for each of the frequency specific sensors may be set in the controller to match the "radiation signature" of a particular type of vegetation. Thus, for example, a particular plant may have a unique "radiation signature" determined by its absorption of electromagnetic radiation at two selected frequencies in the IR and visible bands respectively. The controller has the capability of reading the output signals from any number of sensors in the sensor head simultaneously, with a unique decision window being set for each sensor. The controller preferably operates in a "continuous read mode". This means there are no speed limitations or restrictions on data throughput.

Figure 9:
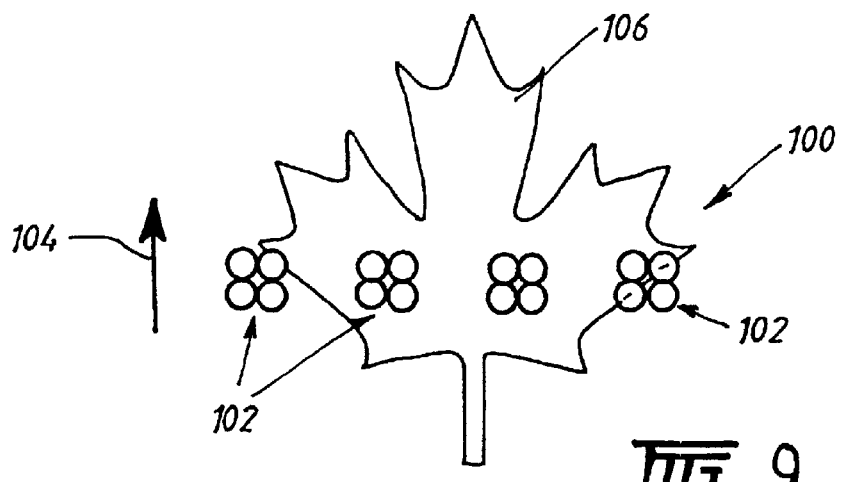

FIG. 9 illustrates another possible sensor array 100 having a geometric configuration of sensors 102 which is a combination of the configurations illustrated in FIGS. 7(a) and 8(a). Sensor array 100 comprises a linear array of four groups of four sensors 104 spaced at 25 mm centres. Such an array can provide multiple readings of reflected radiation from a broadleaf plant, thus increasing the reliability of the sensor assembly. Arrow 104 indicates the direction of travel of the device.

More compact sensor arrays can be employed. Such arrays create a very small read footprint on the target vegetation which enables weeds to be detected earlier in the growing season. Selective spraying of weeds can be incorporated earlier in the season, leading to greater reduction in herbicide usage. Decision windows may be set in the logic controller for each sensor in the array depending on the type of vegetation it is desired to discriminate. The smaller sensors allow for a number of readings to be taken from the same target vegetation allowing for more accurate determination of the type of plant.

Now that embodiments of the device for distinguishing different types of ground vegetation and a boom spray which incorporates the device, have been described in detail, it will be apparent that the device provides significant advantages over prior art arrangements, including but not limited to the following:

(a) Distinguishing of different types of ground vegetation or coverage can be effected independently of ambient light conditions;

(b) Signal processing is very rapid as only a single comparison of values need be made, thus facilitating rapid decision making on-the-fly;

(c) No speed monitoring is required as each spray nozzle is activated for the duration of sensing the presence of a weed in the target area only;

(d) The volume per acre of herbicide required is vastly reduced as the application of herbicide can be precisely targeted to weeds only. Refilling of the tank on the boom spray is also minimised.

Numerous variations and modifications will suggest themselves to persons skilled in the relevant arts, in addition to those already described, without departing from the basic inventive concepts. For example, a circular configuration of sensors in the sensor array may provide advantages in detecting certain types of vegetation. All such variations and modifications are to be considered within the scope of the present invention, the nature of which is to be determined from the foregoing description and the appended claims.

What is claimed is:

1. A device for discriminating different types of ground vegetation, the device comprising:

an artificial source of electromagnetic radiation for directing a beam of radiation onto the vegetation;

a plurality of sensors for detecting radiation from said radiation source reflected onto each of said sensors from the vegetation in a selected frequency band and generating a sensing signal from each sensor in response to said detection, and wherein said plurality of sensors are arranged in a sensor array with a geometric configuration adapted to aid in discriminating different types of vegetation;

signal processing means for determining whether a magnitude of each said sensing signal falls within a predetermined range of values whereby, in use, one type of vegetation can be distinguished from another type based on the magnitudes of said sensing signals; and, a shroud comprising a sheet of flexible, light-impervious material of sufficient length so as to extend to a height of between 10 to 500 mm above the target vegetation whereby, in use, said shroud minimises the amount of sunlight reflected from the vegetation.

2. A device for discriminating different types of ground vegetation as defined in claim 1, further comprising a sensor assembly for focusing the reflected radiation onto said plurality of sensors, said assembly including a plurality of lenses arranged to focus the reflected radiation in such a manner that the sensors always "see" a read footprint on the target vegetation of substantially constant size irrespective of the distance between the sensor assembly and the vegetation.

3. A device for discriminating different types of ground vegetation as defined in claim 2, wherein said sensor assembly further comprises an elongate tube having said plurality of lenses precisely located at predetermined positions along the length of the tube, and a plurality of buffers adapted to prevent the reflection of radiation from an inner wall of the tube into the sensors whereby, in use, focussing of the reflected radiation can be obtained which results in substantially no detectable variation in the size of the read footprint on the target vegetation when the distance between the sensor assembly and the target vegetation is varied.

4. A device for discriminating different types of ground vegetation as defined in claim 1, wherein said source of electromagnetic radiation is a wide-spectrum incandescent lamp capable of directing a beam of radiation with wavelengths in the visible and the infra-red regions of the electromagnetic spectrum.

5. A device for discriminating different types of ground vegetation as defined in claim 1, wherein said sensor is provided with a filter for passing radiation in said selected frequency band to the sensor.

6. A device for discriminating different types of ground vegetation as defined in claim 1, wherein each sensor is adapted to detect radiation in a different selected frequency band.

7. A device for discriminating different types of ground vegetation as defined in claim 1, wherein said selected frequency band is in the visible and infra-red portion of the spectrum having a wavelength within the range of 450 nm to 10 $\mu$m.

8. A device for discriminating different types of ground vegetation as defined in claim 7, wherein said selected frequency band is in the visible and near infra-red waveband of approximately 650 nm to 2000 nm.

9. A device for discriminating different types of ground vegetation as defined in claim 1, wherein said plurality of sensors are arranged in a linear array comprising a row of at least three sensors such that the image of a single stem or leaf of a target vegetation falls between the read footprint of the outer two sensors, which allows discrimination of plants either similar, smaller or larger than the target vegetation.

10. A device for discriminating different types of ground vegetation as defined in claim 1, wherein said signal processing means determines whether a magnitude of the sensing signal falls within a predetermined range of values (a sensing window) which is specific to each sensor in the sensor array.

11. A device for discriminating different types of ground vegetation as defined in claim 10, wherein each sensor in the sensor array has a sensing window that is unique to that sensor.

12. A device for discriminating different types of ground vegetation as defined in claim 1, wherein said artificial radiation source produces a beam of substantially collimated light.

13. A device for discriminating different types of ground vegetation as defined in claim 12, further comprising a parabolic mirror provided adjacent said radiation source for producing a beam of substantially collimated light.

14. A device for discriminating different types of ground vegetation as defined in claim 13, wherein said radiation source is an LED.

15. A device for discriminating different types of ground vegetation as defined in claim 14, wherein said LED provides electromagnet radiation in the infra-red wave band.

16. An agricultural spraying apparatus for spraying ground vegetation, the apparatus comprising:

a spraying means for delivering a liquid spray to ground vegetation;

an artificial source of electromagnetic radiation for directing a beam of radiation onto the vegetation a plurality of sensors for detecting radiation from said radiation source reflected onto each of said sensors from the vegetation in a selected frequency band and generating a sensing signal from each sensor in response to said detection, and wherein said plurality of sensors are arranged in a sensor array with a geometric configuration adapted to aid in discriminating different types of vegetation;

signal processing means operatively connected to said sensor array and spraying means for determining whether a magnitude of each said sensing signal falls within a predetermined range of values, and for actuating said spraying means when a particular type of vegetation is distinguished from another type based on the magnitudes of said sensing signals; and, a shroud comprising a sheet of flexible, light-impervious material of sufficient length so as to extend to a height of between 10 to 500 mm above the target vegetation whereby, in use, said shroud minimises the amount of sunlight reflected from the vegetation.

17. An agricultural spraying apparatus as defined in claim 16, wherein said spraying means includes a plurality of spray nozzles and a corresponding plurality of electromagnetically actuated valves for controlling the delivery of said liquid spray through each nozzle.

18. An agricultural spraying apparatus as defined in claim 17, where in said radiation source and sensor array are one set of a plurality of sets of radiation sources and sensor arrays, a respective set being provided adjacent each of said spray nozzles.

19. An agricultural spraying apparatus as defined in claim 16, further comprising sensor assembly for focusing the reflected radiation onto said plurality of sensors, said assembly including a plurality of lenses arranged to focus the reflected radiation in such a manner that the sensors always "see" a read footprint on the target vegetation of substantially constant size irrespective of the distance between the sensor assembly and the vegetation.

20. An agricultural spraying apparatus as defined in claim 19, wherein said sensor assembly further comprises an elongate tube having said plurality of lenses precisely located at predetermined positions along the length of the tube, and a plurality of buffers adapted to prevent the reflection of radiation from an inner wall of the tube into the sensors whereby, in use, focussing of the reflected radiation can be obtained which results in substantially no detectable variation in the size of the read footprint on the target vegetation when the distance between the sensor assembly and the target vegetation is varied.

* * * * *

UNITED STATES PATENT AND TRADEMARK OFFICE
CERTIFICATE OF CORRECTION

PATENT NO. : 6,443,365 B1
DATED : September 3, 2002
INVENTOR(S) : Robert M. Tucker and Christopher C. Scott It is certified that error appears in the above-identified patent and that said Letters Patent is hereby corrected as shown below:

<u>Title page,</u>
Item [57], ABSTRACT,
Line 12, please delete "infred" and insert -- infra-red -- therefor.

Signed and Sealed this

Fourteenth Day of September, 2004

JON W. DUDAS
*Director of the United States Patent and Trademark Office*